United States Patent [19]

Sauer

[11] Patent Number: 5,833,677
[45] Date of Patent: Nov. 10, 1998

[54] ABSORBENT ARTICLE HAVING A CONTAINMENT DAM

[75] Inventor: Barbara Oakley Sauer, Fremont, Wis.

[73] Assignee: Kimberly-Clark Worldwide, Inc., Neenah, Wis.

[21] Appl. No.: 706,581

[22] Filed: Sep. 5, 1996

[51] Int. Cl.⁶ .................................................. A61F 13/15
[52] U.S. Cl. ...................... 604/369; 604/378; 604/385.1; 604/385.2
[58] Field of Search ............................ 604/385.1, 385.2, 604/378, 369

[56] References Cited

U.S. PATENT DOCUMENTS

| | | |
|---|---|---|
| 810,122 | 1/1906 | Green . |
| 810,123 | 1/1906 | Green . |
| 810,125 | 1/1906 | Green . |
| 810,130 | 1/1906 | Green . |
| 3,572,342 | 3/1971 | Lindquist et al. ....................... 604/369 |
| 3,592,194 | 7/1971 | Duncan ................. 604/385.1 |
| 4,257,418 | 3/1981 | Hessner . |
| 4,610,682 | 9/1986 | Kopp ........................ 604/385.1 |
| 4,662,877 | 5/1987 | Williams . |
| 4,681,577 | 7/1987 | Stern et al. ............................. 604/378 |
| 4,762,521 | 8/1988 | Roessler et al. . |
| 4,778,459 | 10/1988 | Fuisz ....................................... 604/378 |
| 4,798,603 | 1/1989 | Meyer et al. ........................... 604/378 |
| 4,892,536 | 1/1990 | DesMarais et al. .................. 604/385.2 |
| 4,895,568 | 1/1990 | Enloe ................................... 604/385.2 |
| 4,950,262 | 8/1990 | Takagi .................................. 604/385.1 |
| 4,990,147 | 2/1991 | Freeland ............................... 604/385.2 |
| 5,026,364 | 6/1991 | Robertson ............................. 604/385.1 |
| 5,027,662 | 7/1991 | James ................................... 604/385.2 |
| 5,062,840 | 11/1991 | Holt et al. ............................. 604/385.1 |
| 5,171,236 | 12/1992 | Dreier et al. .......................... 604/369 |
| 5,176,668 | 1/1993 | Bernardin ................................ 604/368 |
| 5,176,672 | 1/1993 | Bruemmer et al. ................... 604/385.1 |
| 5,192,606 | 3/1993 | Proxmire et al. ........................ 428/284 |
| 5,207,663 | 5/1993 | McQueen .............................. 604/385.1 |
| 5,269,775 | 12/1993 | Freeland et al. ...................... 604/385.2 |
| 5,281,208 | 1/1994 | Thompson et al. ..................... 604/378 |
| 5,300,053 | 4/1994 | Genaro ................................... 604/378 |
| 5,304,159 | 4/1994 | Tanji et al. ............................. 604/385.2 |
| 5,304,160 | 4/1994 | Igaue et al. ............................ 604/385.2 |
| 5,306,266 | 4/1994 | Freeland ................................ 604/385.1 |
| 5,330,459 | 7/1994 | Lavon et al. ........................... 604/385.1 |
| 5,330,598 | 7/1994 | Erdman et al. ........................... 156/164 |
| 5,344,516 | 9/1994 | Tanji et al. ............................... 156/164 |
| 5,356,405 | 10/1994 | Thompson et al. ....................... 604/384 |

(List continued on next page.)

FOREIGN PATENT DOCUMENTS

| | | |
|---|---|---|
| 0585964 | 3/1994 | European Pat. Off. ............ 604/385.2 |
| 0692231 A1 | 1/1996 | European Pat. Off. . |
| 949179 | 11/1994 | South Africa . |
| 949262 | 11/1994 | South Africa . |
| 2284537 | 6/1995 | United Kingdom . |
| 2284538 | 6/1995 | United Kingdom . |
| 2284550 | 6/1995 | United Kingdom . |
| 2287393 | 9/1995 | United Kingdom . |
| 9414395 | 7/1994 | WIPO ................................ 604/385.1 |
| 96/01609 | 1/1996 | WIPO . |
| 96/17570 A1 | 6/1996 | WIPO . |

OTHER PUBLICATIONS

Patent Cooperation Treaty Search Report from the International Search Authority, International Application No. PCT/US 97/12450 dated Nov. 28, 1997.

*Primary Examiner*—John G. Weiss
*Assistant Examiner*—K. M. Reichle
*Attorney, Agent, or Firm*—Jeffrey B. Curtin

[57] ABSTRACT

An absorbent article includes a compression resistant containment dam which is configured to inhibit the longitudinal flow of fecal material along the body facing surface of the absorbent article. The containment dam is positioned in a laterally extending direction and is located on the body facing surface of the absorbent article such that, when the absorbent article is being worn by a wearer sitting on a flat surface, the containment dam is positioned along a line where the wearer's buttocks depart from the flat surface. The containment dam defines a relatively high resistance to compression for improved performance.

33 Claims, 5 Drawing Sheets

U.S. PATENT DOCUMENTS

| | | | |
|---|---|---|---|
| 5,366,453 | 11/1994 | Zehner et al. | 604/385.2 |
| 5,391,160 | 2/1995 | Runeman et al. | 604/378 |
| 5,409,476 | 4/1995 | Coates | 604/391 |
| 5,417,680 | 5/1995 | Kimura et al. | 604/385.2 |
| 5,439,458 | 8/1995 | Noel et al. | 604/378 |
| 5,439,459 | 8/1995 | Tanji et al. | 604/385.2 |
| 5,451,442 | 9/1995 | Pieniak et al. | 428/54 |
| 5,509,915 | 4/1996 | Hanson et al. | 604/378 |
| 5,514,121 | 5/1996 | Roe et al. | 604/385.1 |
| 5,558,660 | 9/1996 | Droer | 604/378 |
| 5,601,545 | 2/1997 | Glaug et al. | 604/385.2 |
| 5,653,703 | 8/1997 | Roe et al. | 604/385.1 |

ABSORBENT ARTICLE HAVING A CONTAINMENT DAM

BACKGROUND OF THE INVENTION

1. Field of the Invention

The present invention relates to an absorbent article for absorbing body fluids and exudates, such as urine and fecal material. More particularly, the present invention relates to absorbent garments, such as disposable diapers and adult incontinence garments, which are configured to collect and contain fecal material and avoid leakage.

2. Description of the Related Art

Conventional absorbent articles, such as disposable diapers, employ absorbent materials located between a liquid pervious topsheet and a liquid impermeable backsheet to absorb body exudates. Such conventional absorbent articles have also typically included elasticized waistbands and leg cuffs to help reduce the leakage of body exudates.

However, many of such conventional absorbent articles have not been completely satisfactory. For example, many conventional absorbent articles have not completely contained the body exudates within the article during use thereby undesirably resulting in leakage which has soiled the clothes of the wearer. This leakage problem has been particularly evident in the waist margins of such absorbent articles when runny or watery fecal material has been excreted by the wearer during use. Typically, the runny or watery fecal material has been forced longitudinally outwards from the crotch of the article due to the forces exerted by the wearer. Such problems are magnified when the wearer is particularly active and continually exerts pressure on the crotch area of the article. The leakage problem has also occurred because the excreted fecal material has had an affinity for the skin. As a result, such fecal material has traveled along the skin of the wearer and has not been sufficiently contained and controlled within the absorbent articles.

Some conventional absorbent articles have included elasticized components and containment or barrier flaps at the waist sections of the article to reduce such leaks. However, such elasticized components and containment flaps have not completely eliminated all leakage from the waist sections of such articles. For example, exudates such as runny fecal material have remained on and been transferred along the skin of the wearer until they escape through small openings between the containment flaps and the body of the wearer. Such openings between the body of the wearer and the containment flaps have been caused by improper fit of the article about the wearer and the movements of the wearer during use.

As a result, although such waist elastics and containment flaps have improved the performance of such articles, there remains a need to further reduce the number of leaks and, in particular, the number of leaks of fecal material from the waist sections of such absorbent articles.

SUMMARY OF THE INVENTION

In response to the difficulties and problems discussed above, a new disposable absorbent article which has a containment dam for containing and stopping the longitudinal flow of fecal material has been discovered.

As used herein, the term "compression resistance" refers to the compression resistance value determined according to the Compression Resistance Test set forth below.

In one aspect, the present invention relates to a disposable absorbent article which includes a laterally extending, compression resistant containment dam. The containment dam is configured to inhibit the longitudinal flow of fecal material along the bodyfacing surface of the absorbent article. The containment dam is located on the bodyfacing surface of the absorbent article such that, when the absorbent article is being worn by a wearer sitting on a flat surface, the laterally extending containment dam is positioned along a line of departure between said wearer's buttocks and said flat surface. In a particular aspect, the containment dam is located inwardly from an end edge of the absorbent article a distance which is at least about 10 percent of a length of the absorbent article. Desirably, the containment dam defines a compression resistance of at least about 50 percent and a width to height ratio of at least about 0.5.

The absorbent article may further include an attachment means such as a sheet of material for securing and stabilizing the containment dam. The attachment means is configured to maintain the containment dam in an upright position during use.

In another aspect, the present invention relates to an absorbent article having a front waist section, a rear waist section, an intermediate section which interconnects the front and rear waist sections, a pair of longitudinally opposed end edges, and a pair of laterally opposed side edges. The article includes a backsheet layer; a liquid permeable topsheet layer which is connected in superposed relation to the backsheet layer; and an absorbent body which is located between the topsheet layer and the backsheet layer. The article also includes a compression resistant, containment dam which is located on the topsheet layer longitudinally inward from the end edge in the rear waist section of the absorbent article a distance of at least about 10 percent of a length of the absorbent article. The containment dam defines a compression resistance of at least about 50 percent and is configured to inhibit a longitudinal flow of fecal material along the topsheet layer of the absorbent article. In a particular aspect, the distance the containment dam is located from the end edge of the absorbent article is at least about 5.0 centimeters.

In yet another aspect, the present invention relates to an absorbent article which includes a backsheet layer; a liquid permeable topsheet layer which is connected in superposed relation to the backsheet layer; an absorbent body which is located between the topsheet layer and the backsheet layer; a compression resistant containment dam; and a first absorbent sheet located on the topsheet adjacent the containment dam. The compression resistant, containment dam is located on the topsheet longitudinally inward from the end edge in the rear waist section of the absorbent article. The containment dam is configured to inhibit the longitudinal flow of fecal material along the topsheet layer of the absorbent article. The first absorbent sheet may be located on the topsheet layer between the containment dam and the lateral centerline of the absorbent article. The absorbent sheet layer is configured to dewater the fecal material to further inhibit the flow of fecal material along the topsheet layer. In a particular aspect, the absorbent article also includes a second absorbent sheet which is located on the topsheet layer between the containment dam and the end edge in the rear waist section of the absorbent article.

The various aspects of the present invention can advantageously provide an absorbent article which effectively absorbs and contains body exudates. In particular, the present invention removes exudates such as runny fecal material from the skin of the wearer and prevents or at least slows down the longitudinal flow of fecal exudates such that the fecal material can be effectively contained in portions of the article configured to provide such containment. As a result, the absorbent articles of the various aspects of the present invention have reduced leakage when compared to conventional absorbent articles which results in improved consumer preference.

BRIEF DESCRIPTION OF THE DRAWINGS

The invention will be more fully understood and further advantages will become apparent when reference is made to the following detailed description of the invention and the accompanying drawings, in which.

DETAILED DESCRIPTION OF THE INVENTION

The following detailed description will be made in the context of a disposable diaper article which is adapted to be worn by infants about the lower torso. It is readily apparent, however, that the absorbent article of the present invention would also be suitable for use as other types of absorbent articles, such as feminine care pads, incontinence garments, training pants, and the like. In addition, the invention will be described in the context of its various configurations. It should be appreciated that alternative arrangements of the invention can comprise any combination of such configurations.

Figure 1:
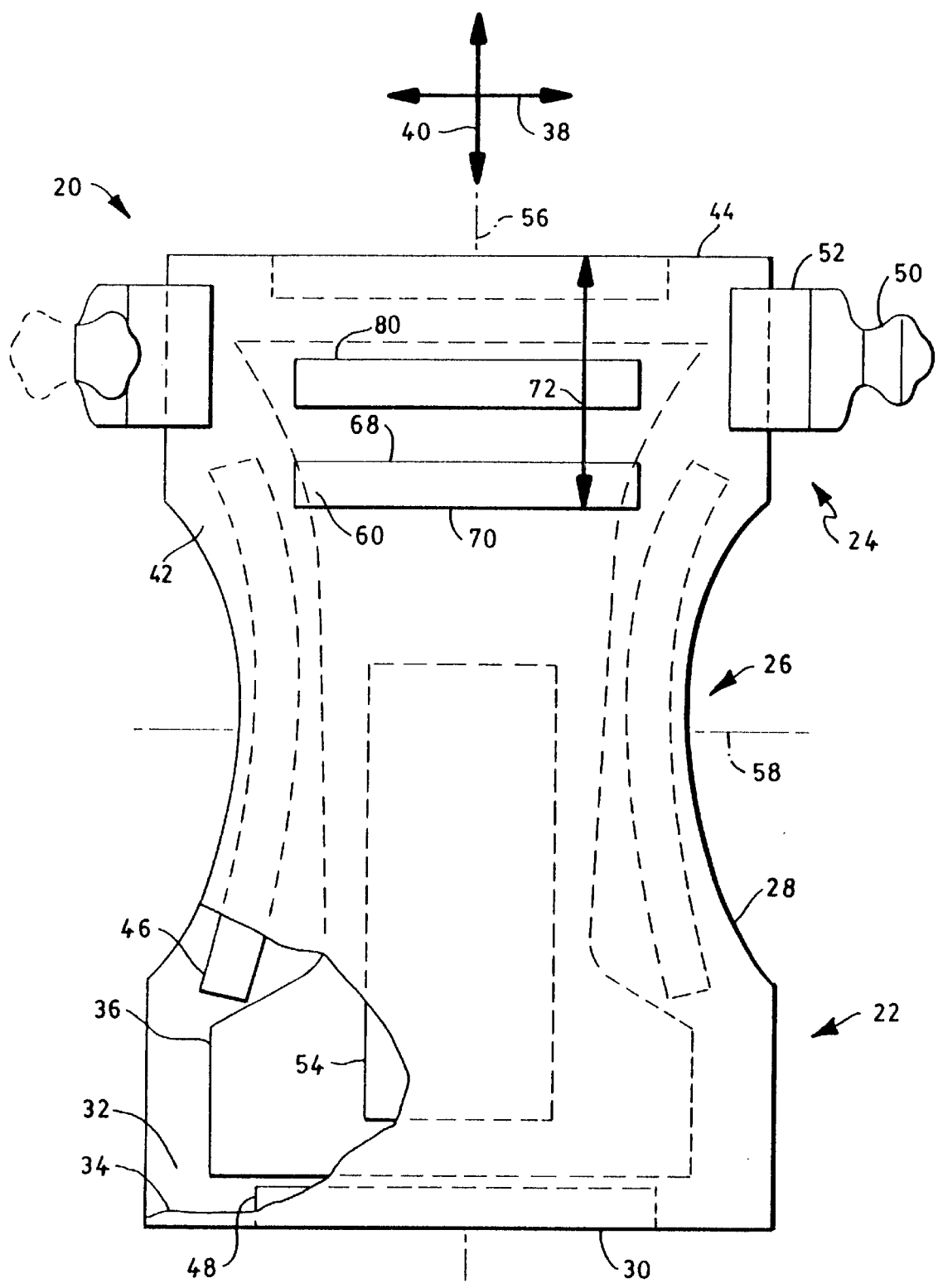
FIG. 1 representatively shows a partially cut away, top plan view of an absorbent article according to one embodiment of the invention.
Figure 2:
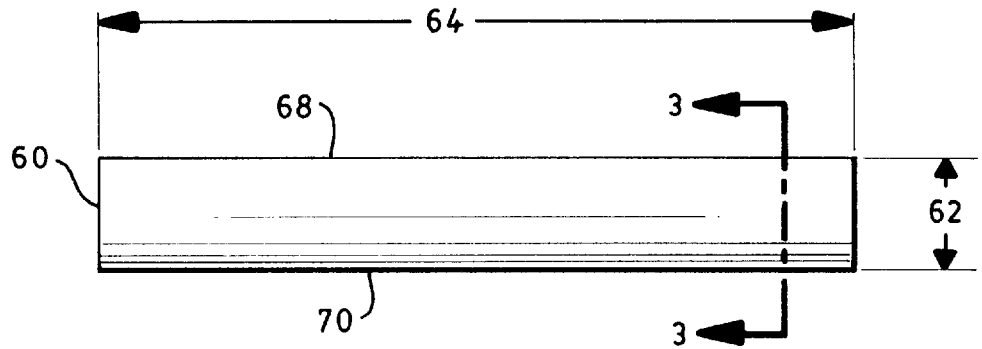
FIG. 2 representatively shows an exploded top plan view of the containment dam of the absorbent article of FIG. 1.
Figure 3A:
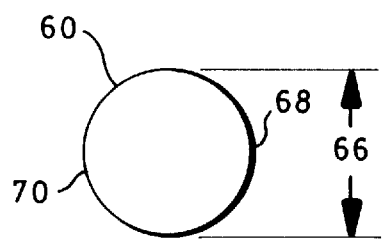
FIG. 3A representatively shows a sectional view of the absorbent article of FIG. 2 taken along line 3—3.

With reference to FIGS. 1–3, an integral absorbent garment article, such as the disposable diaper 20, generally defines a front waist section 22, a rear waist section 24, an intermediate section 26 which interconnects the front and rear waist sections, a pair of laterally opposed side edges 28, and a pair of longitudinally opposed end edges 30. The front and rear waist sections include the general portions of the article which are constructed to extend substantially over the wearer's front and rear abdominal regions, respectively, during use. The intermediate section of the article includes the general portion of the article which is constructed to extend through the wearer's crotch region between the legs. The opposed side edges 28 define leg openings for the diaper and generally are curvilinear or contoured to more closely fit the legs of the wearer. The opposed end edges 30 define a waist opening for the diaper 20 and typically are straight but may also be curvilinear.

FIG. 1 is a representative plan view of the diaper 20 of the present invention in a flat, uncontracted state. Portions of the structure are partially cut away to more clearly show the interior construction of the diaper 20, and the surface of the diaper which contacts the wearer is facing the viewer. The diaper 20 includes a substantially liquid impermeable backsheet 32, a porous, liquid permeable topsheet 34 positioned in facing relation with the backsheet 32, and an absorbent body 36, such as an absorbent pad, which is located between the backsheet and the topsheet. The diaper 20 also defines a lateral direction 38 and a longitudinal direction 40 and a longitudinal centerline 56 and a lateral centerline 58. Marginal portions of the diaper 20, such as marginal sections of the backsheet 32, may extend past the terminal edges of the absorbent body 36. In the illustrated embodiment, for example, the backsheet 32 extends outwardly beyond the terminal marginal edges of the absorbent body 36 to form side margins 42 and end margins 44 of the diaper 20. The topsheet 34 is generally coextensive with the backsheet 32 but may optionally cover an area which is larger or smaller than the area of the backsheet 32, as desired.

To provide improved fit and to help reduce leakage of body exudates from the diaper 20, the side margins 42 and end margins 44 of the diaper may be elasticized with suitable elastic members, such as leg elastic members 46 and waist elastic members 48. For example, the leg elastic members 46 may include single or multiple strands of elastic or elastomeric composites which are constructed to operably gather and shirr the side margins 42 of the diaper 20 to provide elasticized leg bands which can closely fit around the legs of the wearer to reduce leakage and provide improved comfort and appearance. Similarly, the waist elastic members 48 can be employed to elasticize the end margins 44 of the diaper 20 to provide elasticized waistbands. The waist elastics are configured to operably gather and shirr the waistband sections to provide a resilient, comfortably close fit around the waist of the wearer.

The elastic members 46 and 48 are secured to the diaper 20 in an elastically contractible condition so that in a normal under strain configuration, the elastic members effectively contract against the diaper 20. For example, the elastic members 46 and 48 may be elongated and secured to the diaper 20 while the diaper is in an uncontracted condition. In FIG. 1, the elastic members 46 and 48 are illustrated in their uncontracted, stretched condition for the purpose of clarity. Alternatively, the diaper 20 may include a pair of separate, elasticized and gathered leg gussets (not shown) which are attached to the diaper along the side margins 42 in at least the intermediate section 26 of the diaper 20 to provide elasticized leg cuffs. Such leg gussets may be configured to extend beyond and bridge across the respective concave portion of the side margins 42.

The diaper 20, as representatively illustrated in FIG. 1, may further include a pair of fasteners 50 which are employed to secure the diaper 20 about the waist of a wearer. Suitable fasteners 50 include hook-and-loop type fasteners, adhesive tape fasteners, buttons, pins, snaps, mushroom-and-loop fasteners, and the like. A cooperating side panel member 52 can be associated with each fastener and may be constructed to be nonelasticized, or to be elastically stretchable at least along the lateral direction 38 of the diaper 20.

The diaper 20 may also include a pair of elasticized, longitudinally extending containment flaps (not shown) which are configured to maintain an upright, perpendicular arrangement in at least the intermediate section 26 of the diaper 20 to serve as an additional barrier to the lateral flow of body exudates. The diaper 20 may further include a surge management layer 54 positioned between the topsheet 34 and the absorbent body 36 which is configured to efficiently hold and distribute liquid exudates to the absorbent body 36. The surge management layer 54 can prevent the liquid exudates from pooling and collecting on the portion of the diaper positioned against the wearer's skin, thereby reducing the level of skin hydration. Suitable constructions and arrangements of containment flaps and surge management layers are well known to those skilled in the art. Other suitable diaper components may also be incorporated on absorbent articles of the present invention.

The diaper 20, as representatively illustrated in FIGS. 1–3, further includes at least one containment dam 60 which is desirably located on the bodyfacing surface of the topsheet 34. For example, the diaper 20 may include from 1 to about 3 containment dams which are laterally aligned in the diaper 20. The containment dam 60 is configured to remove exudates such as runny fecal material from the skin of the wearer and inhibit the longitudinal flow of fecal exudates into regions of the diaper 20 such as the rear waist section 24 to more effectively contain such material within the diaper 20.

The diaper 20 may be of various suitable shapes. For example, the diaper may have an overall rectangular shape, T-shape or an approximately hour-glass shape. In the shown embodiment, the diaper 20 has a generally I-shape. Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al.; and U.S. Pat. No. 5,509,915 issued Apr. 23,1996, to Hanson et al., the disclosures of which are herein incorporated by reference to the extent they are consistent herewith. The various aspects and configurations of the invention can provide distinctive combinations of softness, body conformity, reduced red-marking of the wearer's skin, reduced skin hydration, and improved containment of body exudates.

The various components of the diaper 20 are integrally assembled together employing various types of suitable attachment means, such as adhesive, sonic bonds, thermal bonds or combinations thereof. In the shown embodiment, for example, the topsheet 34 and backsheet 32 are assembled to each other and to the absorbent body 36 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the elastic members 46 and 48 and the fasteners 50, may be assembled into the diaper 20 article by employing the above-identified attachment mechanisms.

The backsheet 32 of the diaper 20, as representatively illustrated in FIG. 1, may suitably be composed of a material which is either liquid permeable or liquid impermeable. It is generally preferred that the backsheet 32 be formed from a material which is substantially impermeable to liquids. For example, a typical backsheet can be manufactured from a thin plastic film or other flexible liquid-impermeable material. For example, the backsheet 32 may be formed from a polyethylene film having a thickness of from about 0.012 millimeter (0.5 mil) to about 0.051 millimeter (2.0 mils). If it is desired to present the backsheet with a more clothlike feeling, the backsheet 32 may comprise a polyolefin film having a nonwoven web laminated to the outer surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers, which fibers have a thickness of about 1.5 to 2.5 denier per filament, which nonwoven web has a basis weight of about 17 grams per square meter (0.5 ounce per square yard). Methods of forming such clothlike backsheets are known to those skilled in the art.

Further, the backsheet 32 may be formed of a woven or nonwoven fibrous web layer which has been totally or partially constructed or treated to impart a desired level of liquid impermeability to selected regions that are adjacent or proximate the absorbent body 36. Still further, the backsheet 32 may optionally be composed of a micro-porous "breathable" material which permits vapors to escape from the absorbent body 36 while still preventing liquid exudates from passing through the backsheet 32. The backsheet 32 typically provides the outer cover of the diaper 20. The backsheet 32 can also be embossed or otherwise provided with a matte finish to provide a more aesthetically pleasing appearance.

The topsheet 34, as representatively illustrated in FIG. 1, suitably presents a bodyfacing surface which is compliant, soft feeling, and nonirritating to the wearer's skin. Further, the topsheet 34 may be less hydrophilic than the absorbent body 36, to present a relatively dry surface to the wearer, and may be sufficiently porous to be liquid permeable, permitting liquid to readily penetrate through its thickness. A suitable topsheet 34 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet 34 is suitably employed to help isolate the wearer's skin from liquids held in the absorbent body 36.

Various woven and nonwoven fabrics can be used for the topsheet 34. For example, the topsheet may be composed of a meltblown or spunbonded web of polyolefin fibers. The topsheet may also be a bonded-carded web composed of natural and/or synthetic fibers. The topsheet may be composed of a substantially hydrophobic material, and the hydrophobic material may, optionally, be treated with a surfactant or otherwise processed to impart a desired level of wettability and hydrophilicity. In a particular embodiment of the present invention, the topsheet 34 comprises a nonwoven, spunbond, polypropylene fabric composed of about 2.8–3.2 denier fibers formed into a web having a basis weight of about 20 grams per square meter and a density of about 0.13 gram per cubic centimeter. The fabric may be surface treated with about 0.28 weight percent of a surfactant commercially available from the Rohm and Haas Co. under the trade designation TRITON X-102. The surfactant may be applied by any conventional means, such as spraying, printing, brush coating or the like. The surfactant may be applied to the entire topsheet 34 or may be selectively applied to particular sections of the topsheet 34, such as the medial section along the longitudinal centerline of the diaper, to provide greater wettability of such sections.

The absorbent body 36 of the diaper 20, as representatively illustrated in FIG. 1, may suitably comprise a matrix of hydrophilic fibers, such as a web of cellulosic fluff, mixed with particles of a high-absorbency material commonly known as superabsorbent material. In a particular embodiment, the absorbent body 36 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may also be selectively placed into desired zones of the absorbent body 36 to better contain and absorb body exudates. The concentration of the superabsorbent particles may also vary through the thickness of the absorbent body 36. Alternatively, the absorbent body 36 may comprise a laminate of fibrous webs and superabsorbent material or other suitable means of maintaining a superabsorbent material in a localized area.

The absorbent body 36 may have any of a number of shapes. For example, the absorbent core may be rectangular, I-shaped, or T-shaped. It is generally preferred that the absorbent body 36 be narrower in the crotch area than in the front or rear portions of the diaper 20. The size and the absorbent capacity of the absorbent body 36 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent body 36.

Optionally, a substantially hydrophilic tissue wrapsheet (not illustrated) may be employed to help maintain the integrity of the airlaid fibrous structure of the absorbent body 36. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent body. In another aspect of the invention, the wrapsheet material on one side of the absorbent fibrous mass may be bonded to the wrapsheet located on the opposite side of the fibrous mass.

The containment dam 60, as representatively illustrated in FIGS. 1–3, is configured to help reduce leaks along the end edges 30 of the diaper 20 by preventing or at least slowing down the longitudinal flow of fecal exudates into regions of the diaper 20 such as the rear waist section 24 to more effectively contain such material within the diaper 20. The containment dam 60 generally defines a width 62, a length 64, a height 66, a back edge 68, and a front edge 70. Desirably, the containment dam 60 of the different aspects of the present invention is configured to contain substantially all of the solid fecal exudates in the target zone of the diaper 20. As used herein, the term "target zone" refers to that portion of the diaper 20 which is configured to directly receive the insult of fecal exudates from the wearer and generally is located in the crotch portion of the diaper 20. In particular, the target zone may extend from about 5 to about 10 centimeters in length with about one third of it's length extending longitudinally from the lateral centerline 58 of the diaper towards the front waist section 22 of the diaper 20 and the remainder extending longitudinally towards the rear waist section 24 of the diaper 20.

In the illustrated embodiments, a single containment dam 60 is positioned on the topsheet 34 of the diaper 20 between the lateral centerline 58 and the end edge 30 in the rear waist section 24 of the diaper 20. In such a configuration, the containment dam 60 is configured to at least reduce if not eliminate the longitudinal flow of fecal exudates to reduce the leakage of fecal exudates from the rear waist section 24 of the diaper 20. The leakage of fecal exudates from the rear waist section 24 of conventional diapers has been a difficult problem to overcome and has been particularly undesirable to the consumer.

The diaper 20 of the different aspects of the present invention may further include at least one or more additional containment dams to further reduce such longitudinal flow of fecal exudates. For example, as representatively illustrated in FIG. 1, the diaper 20 may include a second containment dam 80 located between the illustrated containment dam 60 and the end edge 30 of the rear waist section 24 of the diaper 20. In a particular embodiment, the diaper 20 of the different aspects of the present invention may include from about 2 to about 4 containment dams 60 arranged in a ladder-type configuration between the lateral centerline 58 and the end edge 30 in the rear waist section 24 of the diaper 20 for improved performance.

In most embodiments, the containment dam 60 is positioned on the bodyfacing surface of the topsheet 34 of the diaper 20. The containment dam 60 may remain substantially unattached to the topsheet 34 or may be attached to the topsheet 34 using conventional means described above such as adhesive. Desirably, the containment dam 60 is secured to the topsheet 34 in a manner which stabilizes the dam 60 and maintains the dam 60 in an upright position during use. Alternatively, the containment dam 60 may be located between the topsheet 34 and the absorbent body 36 of the diaper 20. In such an arrangement, the containment dam 60 may be provided directly by the absorbent body 36 of the diaper 20. For example, the absorbent body 36 may include at least one laterally extending portion which defines a greater thickness or height to provide the containment dam 60 of the different aspects of the present invention.

Figure 4:
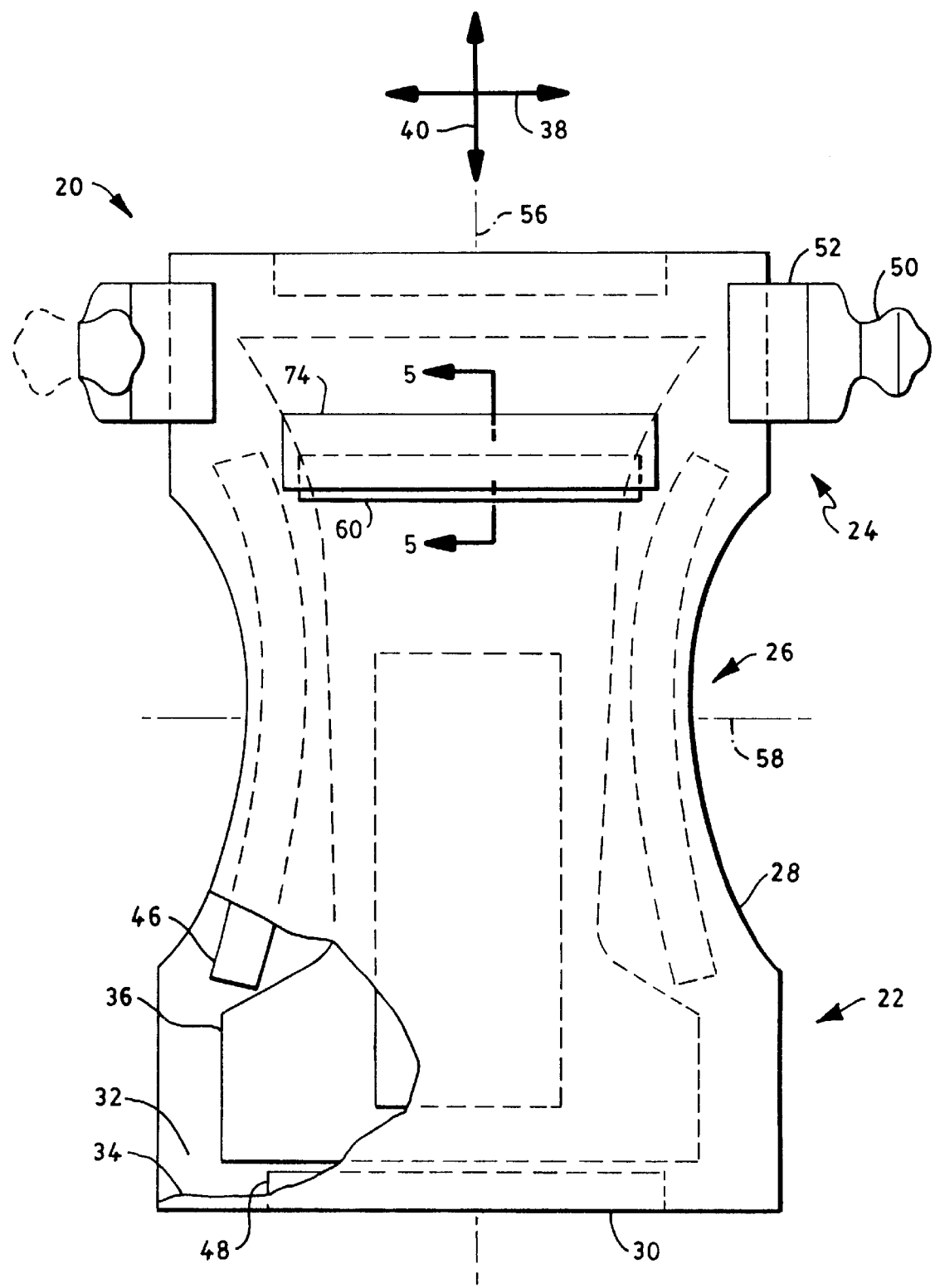
FIG. 4 representatively shows a partially cut away, top plan view of an absorbent article according to another embodiment of the invention.
Figure 5:
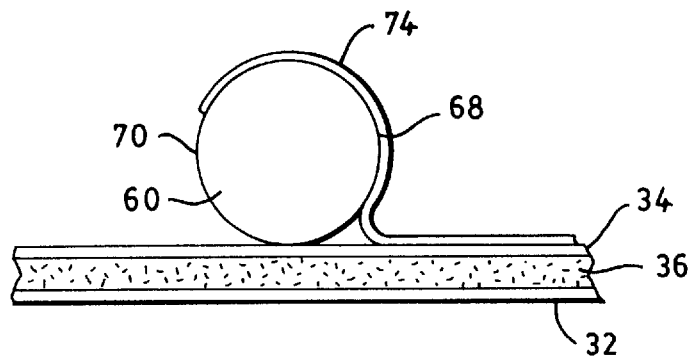
FIG. 5 representatively shows a sectional view of the absorbent article of FIG. 4 taken along line 5—5.

In one embodiment of the present invention as representatively illustrated in FIGS. 4 and 5, the containment dam 60 may be held or anchored in place by one or more sheets of material 74 such as a nonwoven material or foam material which extends at least partially over the bodyfacing surface of the containment dam 60 and which may be attached to the topsheet 34 of the diaper 20. Desirably, the sheet of material 74 conforms to the shape and contour of the containment dam 60 to prevent any gaps from forming between the sheet of material 74 and the containment dam 60. For example, the sheet of material 74 may be adhesively bonded to the outer surface of the containment dam 60 to prevent such gaps. Any gap between the sheet 74 and the dam 60 may undesirably provide a ramp for the fecal exudates to move over the top of the containment dam 60 resulting in increased leakage. The sheet of material 74 may be provided by any material which is relatively soft and strong to anchor the dam 60 in place and provide a cushion between the dam 60 and the body of the wearer. Desirably, the sheet of material 74 is a hydrophobic material such that the sheet 74 is not configured to assist in drawing the fecal exudates over the top of the dam 60 and into the rear waist section 24 of the diaper 20.

Typically, the containment dam 60 is located in the rear waist section 24 or intermediate section 26 of the diaper 20 and extends in the lateral direction 38. Desirably, the containment dam 60 is located such that, when the diaper is being worn by a wearer sitting on a flat surface, the containment dam 60 is positioned along the line of departure between rear of the wearer's buttocks and the flat surface. In such a position, the containment dam 60 provides improved resistance to the explosive longitudinal flow of fecal exudates which may occur along the gluteal fold of the wearer due to the compressive forces exerted by the wearer while sitting. For example as representatively illustrated in FIG. 1, the front edge 70 of the containment dam 60 may be located a distance 72 of at least about 5.0 centimeters, desirably at least about 7.5 centimeters and more desirably at least about 10 centimeters from the end edge 30 in the rear waist section 24 of the diaper 20 towards the front waist section 22 of the diaper 20. Typically, the distance 72 the containment dam 60 is located inwardly from the end edge 30 is from about 5.0 centimeters to about 15.0 centimeters. Such distances generally correspond to a distance of at least about 10 percent and desirably at least about 15 percent of the total length of the article. For example, the distance 72 the containment dam 60 is located inwardly from the end edge 30 may be from about 10 percent to about 45 percent of the total length of the article.

Such a configuration is desirable to allow the containment dam 60 to inhibit the longitudinal flow of fecal material into the rear waist section 24 of the diaper 20 while allowing sufficient space in the rear waist section 24 to contain any fecal material which passes over the dam 60 and between the dam 60 and the wearer's body. If the distance 72 the containment dam 60 is located from the end edge 30 is too small, the fecal exudates may be able to gain sufficient momentum when pressure is exerted to carry over the top of the dam 60. In addition, if such distance 72 is too small, the dam 60 may not remain in close contact with the buttocks of the wearer when the wearer is sitting which may result in a less than optimum seal with the wearer's body. Desirably, the containment dam 60 is located such that it maintains a pressure contact with the wearer's body when the wearer is sitting to create a good seal against the longitudinal flow of fecal exudates.

The containment dam 60 may have any shape which provides the desired inhibition of the longitudinal flow of fecal material. Suitable cross sections for the laterally extending containment dam 60 include circular, semi-circular, oval, elliptical, triangular, rectangular, square, and the like. For example, as representatively illustrated in FIGS. 1–3A, the containment dam 60 may define a tubular shape having a circular cross section. Alternatively, as representatively illustrated in FIG. 3B, the containment dam 60 may have a tear drop cross section or some other cross section wherein the width of the dam is sufficient to assist in maintaining the dam 60 in the upright position.

Figure 3B:
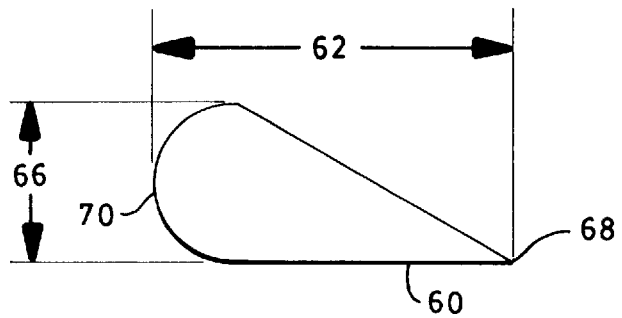
FIG. 3B representatively shows a sectional view of a containment dam according to another embodiment of the invention.

As representatively illustrated in FIGS. 2–3B, the containment dam 60 defines a width 62, a length 64, and a height 66. The width 62 of the containment dam 60 provides stability to the dam 60 such that it does not fold over or bend during use. Desirably, the containment dam defines a width 62 of at least about 0.5 centimeters and more desirably at least about 1.0 centimeters for improved performance.

The length 64 of the containment dam 60 must be sufficient to block at least the majority of the passageways through which the fecal exudates may flow. Desirably, the length 64 of the containment dam is at least sufficient to block the gluteal fold between the buttocks of the wearer. For example, on a diaper article intended to be worn by a medium sized infant, the containment dam 60 may define a length 64 of at least about 2.0 centimeters and desirably at least about 7.5 centimeters. Desirably, the containment dam 60 defines a length which is at least about 10 percent of the width of the diaper 20 as measured along the lateral centerline 58 of the diaper 20. In a particular embodiment, the containment dam 60 defines a length which is substantially equal to the width of the diaper 20 as measured along the lateral centerline 58 of the diaper 20 for improved performance. In another particular embodiment wherein the diaper 20 includes a pair of longitudinally extending containment flaps, the containment dam 60 defines a length which is substantially equal to or less than the width of the diaper 20 between such containment flaps for improved performance.

The height 66 of the containment dam 60 must be sufficient to provide the desired resistance to the longitudinal flow of fecal exudates even when the diaper is subjected to the compressive forces of the wearer. For example, the containment dam 60 may define a height 66 of at least about 0.5 centimeters and desirably at least about 0.75 centimeters.

To maintain the stability of the containment dam 60 during use, the containment dam 60 desirably defines a width to height ratio of at least about 0.5, desirably at least about 0.75, and more desirably at least about 1.0. Width to height ratios less than those set forth above may undesirably result in the containment dam 60 bending or folding over which may result in increased longitudinal flow of fecal exudates over the dam 60. The containment dam 60 may also define an average cross-sectional area of at least about 0.7 square centimeters and desirably at least about 1.0 square centimeters to provide the desired resistance to the flow of fecal exudates.

The containment dam 60 is configured to maintain it's shape during use to effectively inhibit the flow of fecal exudates. For example, it is desirable that the containment dam 60 be capable of resisting any z-directional compressive forces which may be exerted by the wearer during use.

In a particular embodiment, the containment dam 60 defines a z-directional compression resistance of at least about 50 percent, desirably at least about 70 percent, and more desirably at least about 85 percent. For example, the containment dam 60 may define a compression resistance of from about 50 to about 95 percent. When the containment dam has a compression resistance less than the values set forth above, the containment dam may collapse during usage which adversely affects the ability of the dam to resist the longitudinal flow of fecal exudates. Whereas, if the compression resistance of the containment dam is too high, the containment dam may cause undesired redmarking and irritation of the skin of the wearer. Due to the location of the containment dam behind the region of the buttocks which is under the maximum pressure when sitting, such redmarking can be kept to a minimum even with a highly compression resistant material.

Desirably, the containment dam 60 has sufficient compression resilience such that the height 66 of the dam 60 remains at least about 0.3 centimeters and desirably at least about 0.5 centimeters when the containment dam 60 is under a compressive load of about 350 grams per square centimeter.

It is also desirable that the containment dam 60 be flexible such that it readily conforms to the shape and contours of the wearer's buttocks. If the flexibility of the containment dam 60 is too low, the containment dam may not effectively conform to the body of the wearer and may cause undesired leakage and redmarking and irritation of the skin of the wearer. In a particular embodiment, the containment dam 60 may be shaped to conform to the wearer's buttocks to provide improved resistance to the longitudinal flow of exudates. For example, the containment dam 60 may include a raised portion which is configured to ride in the gluteal fold region between the wearer's buttocks to accurately position the dam 60 and inhibit the flow of exudates in the gluteal fold region.

The containment dam 60 of the different aspects of the present invention, as representatively illustrated in FIGS. 1–7, may be made from any material which provides the desired shape and level of compression resistance. Suitable materials include foams, fibrous webs of natural or synthetic fibers or combinations thereof, and multiple layer fibrous webs. For example, the containment dam may be a crosslinked polyethylene foam material which is commercially available from Sentinel Foams, a business having offices located in Hyannis, Mass., under the trade designation EMR NAT.

Figure 7:
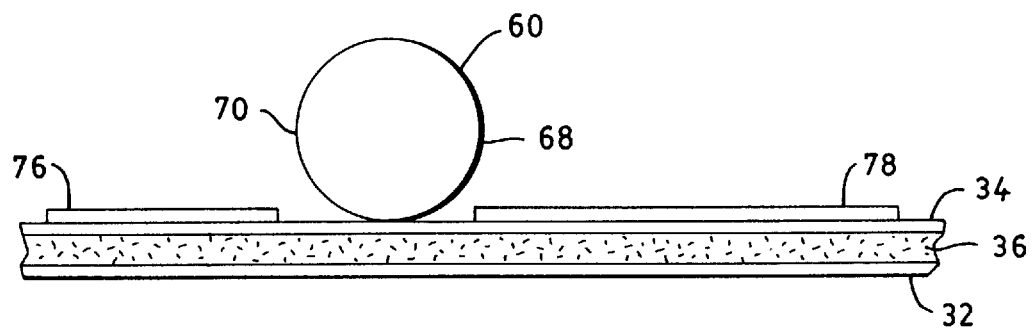
FIG. 7 representatively shows a sectional view of the absorbent article of FIG. 6 taken along line 7—7.
Figure 6:
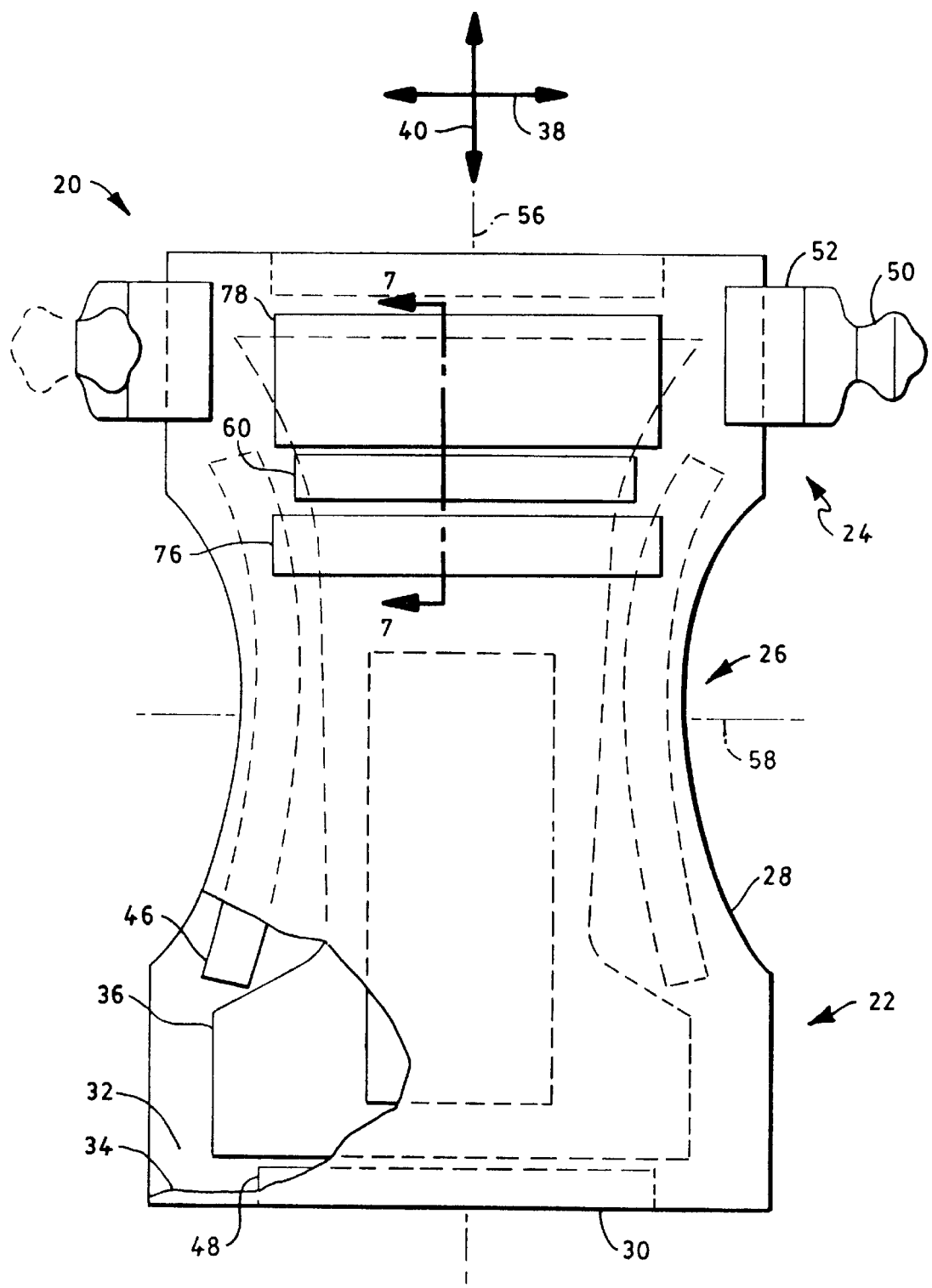
FIG. 6 representatively shows a partially cut away, top plan view of an absorbent article according to another embodiment of the invention.

As representatively illustrated in FIGS. 6 and 7, the diaper 20 of the different aspects of the present invention may further include at least one absorbent sheet 76 located adjacent the containment dam 60. The absorbent sheet is configured to dewater the fecal exudates to further inhibit the longitudinal flow of such exudates to, over and beyond the dam 60. For example, the diaper 20 may include a first absorbent sheet 76 attached to the topsheet 34 adjacent the front edge 70 of the containment dam 60. In such a configuration, the absorbent sheet 76 may be located on the topsheet 34 between the lateral centerline 58 and the containment dam 60 of the diaper 20. The absorbent sheet 76 may be located on the bodyfacing surface of the topsheet 34 or, alternatively, underneath the topsheet 34 as long as the absorbent sheet 76 is capable of at least partially dewatering the fecal material to reduce it's ability to flow over the containment dam 60.

The diaper 20 may further include a second absorbent sheet 78 located on the topsheet 34 adjacent the back edge 68 of the containment dam 60 to dewater any fecal exudates which might pass over the containment dam 60 during use to inhibit the longitudinal flow of such exudates beyond the dam 60 towards the end edge 30 of the diaper 20.

The absorbent sheets 76 and 78 may have any desired shape and size which effectively dewaters at least a portion of the fecal exudates adjacent the containment dam 60. For example, the absorbent sheets 76 and 78 may define a width in the lateral direction which is substantially equal to the length of the containment dam 60. Alternatively, the absorbent sheets 76 and 78 may be larger or smaller than the containment dam 60. The absorbent sheets 76 and 78 may also define a length in the longitudinal direction which provides the desired dewatering of the fecal exudates. For example, the first absorbent sheet 76 may define a length in the longitudinal direction 40 which is at least about 1 percent and desirably from about 3 to about 5 percent of a length of said absorbent article for improved performance. The second absorbent sheet 78 may extend completely from the back edge 68 of the containment dam 60 to the end edge 30 of the diaper 20 in the rear waist section 24 or may be configured to cover any portion of the diaper between the back edge 30 and the dam 60. Desirably, the absorbent sheets 76 and 78 do not extend into the front portion of the intermediate section 26 or the front waist section 22 of the diaper 20 which might adversely affect the ability of the diaper 20 to readily absorb any urine excreted by the wearer.

The absorbent sheets 74 and 76 can be made from many materials well known to those skilled in the art. For example, the absorbent sheets 74 and 76 may be made from high wet strength materials which include synthetic fibers, polymeric fibers, natural fibers such as cellulosic fibers and the like or combinations thereof. In a particular embodiment, the absorbent sheets 74 and 76 comprise an uncreped through air dried material as described in commonly assigned copending U.S. patent application Ser. No. 08/614,420 filed Mar. 8, 1996, in the name of Chen et al. which is a continuation-in-part of U.S. patent application Ser. No. 08/310,186 filed Sep. 21, 1994, in the name of Chen et al., now abandoned, the disclosures of which are hereby incorporated by reference to the extent they are consistent herewith. Desirably, the absorbent sheets 74 and 76 include hydrophilic fibers such as cellulose or rayon fibers for improved absorbency and performance. The absorbent sheets 74 and 76 define a basis weight of from about 10 to about 150 and desirably from about 20 to about 80 grams per square meter to provide the desired absorbency to effectively dewater the fecal exudates for improved containment while maintaining good drape, softness and integrity. In a particular embodiment wherein the absorbent sheets 74 and 76 are hydrophilic in nature, the absorbent sheet 76 desirably does not extend into the front section of the diaper 20 such that the sheet 76 is less likely to be wetted out by urine during use. Thus, the sheet 76 is able to dewater the fecal exudates even when the wearer has previously urinated in the diaper 20. Moreover, since the diaper 20 is not always changed immediately upon urination as opposed to when a bowel movement occurs, it is desirable that the sheet 76 not be wetted during urination to avoid excessive contact of a wetted surface with the skin of the wearer in continued use.

Accordingly, the different aspects of the present invention advantageously provide an absorbent article having improved containment and control of body exudates and, in particular, fecal material. The containment dam of the present invention is resistant to compression and flexible to effectively maintain its shape and inhibit the longitudinal flow of fecal exudates. As a result, such a containment dam may reduce the amount of leaks from absorbent articles which are caused by fecal material sliding longitudinally along the diaper or skin of the wearer and, in particular, along the skin of the wearer in the gluteal fold region between the buttocks of the wearer. As a result, absorbent articles made according to the present invention may have a reduced incidence of leaks in the waist sections and, in particular, the rear waist section of the article.

Compression Resistance Test

This test is configured to measure the compression resistance of materials intended for use as the containment dam according to the present invention. The compression resistance of the materials indicates the ability of the material to maintain it's shape during use.

A sample of the material intended for use as the containment dam is obtained. The compression resistance of the material is tested in a standard compressometer such as that commercially available from Frazier Precision Instrument Company, a business having offices located in Gaithersburg, Md. Initially, the compressometer is calibrated. The sample of material is then placed in the compressometer which includes a foot which defines a diameter of 3.0 inches. The foot is positioned in contact with the sample of material and the original height of the material is measured and recorded. The foot is then lowered until the pressure on the material is 1.0 pounds per square inch. The compressed height of the material is immediately measured and recorded. The compression resistance value of the material sample is then obtained by dividing the compressed height by the original height and multiplying the result by 100 percent.

Having thus described the invention in rather full detail, it will be readily apparent to a person of ordinary skill that various changes and modifications can be made without departing from the spirit of the invention. All of such changes and modifications are contemplated as being within the scope of the present invention as defined by the subjoined claims.

I claim:

1. A disposable absorbent article which defines a longitudinal direction and a lateral direction, said absorbent article futher comprising an absorbent and a laterally extending, compression resistant containment dam integrally assembled therewith, said containment dam being configured to inhibit a longitudinal flow of fecal material along a bodyfacing surface of said absorbent article wherein said containment dam is located on said bodyfacing surface of said absorbent article inwardly from an end edge of said absorbent article a distance which is from about 10 to about 45 percent of a total length of said absorbent article and wherein said containment dam defines a compression resistance of at least about 85 percent as determined according to a Compression Resistance Test set forth in the specification.

2. An absorbent article according to claim 1 wherein said distance said containment dam is located inwardly from said end edge of said absorbent article is at least about 15 percent to about 45 percent of said total length of said absorbent article.

3. An absorbent article according to claim 1 and further comprising a second laterally extending containment dam which is located on said bodyfacing surface longitudinally outward from said first containment dam to further inhibit the longitudinal flow of fecal material along said bodyfacing surface of said absorbent article.

4. An absorbent article according to claim 1 wherein said containment dam defines a width of at least about 0.5 centimeters and a length of at least about 2.0 centimeters.

5. An absorbent article according to claim 1 wherein said containment dam defines a height of at least about 0.5 centimeters.

6. An absorbent article according to claim 1 wherein said containment dam defines a width to height ratio of at least about 0.5.

7. An absorbent article according to claim 1 wherein said containment dam defines a length which is at least about 10 percent of a width of said absorbent article along a lateral centerline of said absorbent article.

8. An absorbent article according to claim 1 wherein said containment dam defines a length which is substantially equal to a width of said absorbent article along a lateral centerline of said absorbent article.

9. An absorbent article according to claim 1 wherein said containment dam comprises a foam material.

10. An absorbent article according to claim 1 wherein said containment dam defines a tubular shape having a circular cross section.

11. An absorbent article according to claim 1 wherein said containment dam defines a tubular shape having a tear drop cross section.

12. An absorbent article according to claim 1 and further comprising an attachment means for securing and stabilizing said containment dam and maintaining said containment dam in an upright position during use.

13. An absorbent article according to claim 12 wherein said attachment means comprises a sheet of material which is attached to said bodyfacing surface of said absorbent article and which extends at least partially over said containment dam.

14. An absorbent article according to claim 13 wherein said sheet of material conforms to said containment dam to prevent any gaps from forming between said sheet of material and said containment dam.

15. An absorbent article having a longitudinal centerline, a lateral centerline, a front waist section, a rear waist section, an intermediate section which interconnects said front and rear waist sections, a pair of longitudinally opposed end edges in respective ones of said front and rear waist sections, and a pair of laterally opposed side edges, said article further comprising:
   a) a backsheet layer;
   b) a liquid permeable topsheet layer which is connected in superposed relation to said backsheet layer;
   c) an absorbent body which is located between said topsheet layer and said backsheet layer; and
   d) a compression resistant, containment dam which is located on said topsheet layer longitudinally inward from said end edge in said rear waist section of said absorbent article a distance of from about 10 to about 45 percent of a total length of said absorbent article wherein said containment dam defines a compression resistance of at least about 85 percent as determined according to a Compression Resistance Test set forth in the specification and wherein said containment dam is configured to inhibit a longitudinal flow of fecal material along said topsheet layer of said absorbent article.

16. An absorbent article according to claim 15 wherein said distance said containment dam is located from said end edge in said rear waist section of said absorbent article is at least about 5.0 centimeters.

17. An absorbent article according to claim 15 wherein said distance said containment dam is located from said end edge in said rear waist section of said absorbent article is from about 5.0 to about 15.0 centimeters.

18. An absorbent article according to claim 15 and further comprising a second laterally extending containment dam which is located on said bodyfacing surface between said first containment dam and said end edge in said rear waist section to further inhibit the longitudinal flow of fecal material along said topsheet layer of said absorbent article.

19. An absorbent article according to claim 15 wherein said containment dam defines a width of at least about 0.5 centimeters and a length of at least about 2.0 centimeters.

20. An absorbent article according to claim 15 wherein said containment dam defines a height of at least about 0.5 centimeters.

21. An absorbent article according to claim 15 wherein said containment dam defines a width to height ratio of at least about 0.5.

22. An absorbent article according to claim 15 wherein said containment dam comprises a foam material.

23. An absorbent article according to claim 15 and further comprising a sheet of material which conforms to said containment dam and extends at least partially over said containment dam to secure and maintain said containment dam in an upright position during use.

24. An absorbent article according to claim 15 wherein said containment dam includes a hydrophobic, nonwoven material covering at least a portion of an outer surface of said containment dam which is configured to be in contact with a wearer's skin in use.

25. An absorbent article having a longitudinal direction, a lateral direction, a front waist section, a rear waist section, an intermediate section which interconnects said front and rear waist sections, a pair of longitudinally opposed end edges in respective ones of said front and rear waist sections, a longitudinal centerline, and a lateral centerline, said article further comprising:
   a) a backsheet layer;
   b) a liquid permeable topsheet layer which is connected in superposed relation to said backsheet layer;
   c) an absorbent body which is located between said topsheet layer and said backsheet layer;
   d) a compression resistant, containment dam which is located on a bodyfacing surface of said topsheet layer between said end edge in said rear waist section of said absorbent article and said lateral centerline of said absorbent article and which is configured to inhibit a longitudinal flow of fecal material along said topsheet layer of said absorbent article, and
   e) a first absorbent sheet which is located on said bodyfacing surface of said topsheet layer between said containment dam and said lateral centerline of said absorbent article and which is configured to dewater the fecal material to further inhibit the flow of fecal material along said topsheet layer.

26. An absorbent article according to claim 25 and further comprising a second absorbent sheet which is located on said topsheet layer between said containment dam and said end edge in said rear waist section of said absorbent article.

27. An absorbent article according to claim 25 wherein said containment dam is located longitudinally inward from said end edge in said rear waist section a distance of at least about 10 percent of a total length of said absorbent article.

28. An absorbent article according to claim 25 wherein said containment dam defines a compression resistance of at least about 50 percent as determined according to a Compression Resistance Test set forth in the specification.

29. An absorbent article according to claim 25 wherein said containment dam defines a width to height ratio of at least about 0.5.

30. An absorbent article according to claim 25 wherein said containment dam comprises a foam material.

31. An absorbent article according to claim 25 wherein said first absorbent sheet comprises a sheet of hydrophilic material.

32. An absorbent article according to claim 25 wherein said first absorbent sheet contains hydrophilic fibers and defines a basis weight of from about 10 to about 150 grams per square meter.

33. An absorbent article according to claim 25 wherein said first absorbent sheet defines a length along said longitudinal centerline of a least about 1 percent of a length of said absorbent article.

* * * * *